United States Patent
Giorgini et al.

(10) Patent No.: US 9,802,192 B2
(45) Date of Patent: Oct. 31, 2017

(54) SORTING CHAMBER FOR MICROSCALE PARTICLES

(75) Inventors: Giuseppe Giorgini, Padua (IT); Gerardo Perozziello, Bologna (IT); Alex Calanca, Mirandola (IT); Gianni Medoro, Casalecchio di Reno (IT); Nicolò Manaresi, Bologna (IT)

(73) Assignee: Menarini Silicon Biosystems S.p.A., Castel Maggiore (IT)

( * ) Notice: Subject to any disclaimer, the term of this patent is extended or adjusted under 35 U.S.C. 154(b) by 1132 days.

(21) Appl. No.: 13/122,169

(22) PCT Filed: Oct. 1, 2009

(86) PCT No.: PCT/IB2009/007010
§ 371 (c)(1),
(2), (4) Date: Oct. 21, 2011

(87) PCT Pub. No.: WO2010/038141
PCT Pub. Date: Apr. 8, 2010

(65) Prior Publication Data
US 2012/0028349 A1    Feb. 2, 2012

(30) Foreign Application Priority Data
Oct. 2, 2008  (IT) .............................. BO2008A0602

(51) Int. Cl.
*B01L 3/00*   (2006.01)
*G01N 1/40*   (2006.01)
(Continued)

(52) U.S. Cl.
CPC ...... *B01L 3/502753* (2013.01); *G01N 1/4077* (2013.01); *B01L 2200/0647* (2013.01);
(Continued)

(58) Field of Classification Search
CPC ......... B01L 3/502753; B01L 3/502761; B01L 2200/0647; B01L 2200/0652;
(Continued)

(56) References Cited

U.S. PATENT DOCUMENTS 6,190,919 B1 *  2/2001  Mastny et al. .................. 436/63
7,056,430 B1    6/2006  Osipchuk et al.
(Continued)

FOREIGN PATENT DOCUMENTS

WO    WO-03/056330 A2    7/2003
WO    WO-2006/108101 A2   10/2006

OTHER PUBLICATIONS

Machine language translation of WO 2003/056330 A2, obtained from google.com/patents on Feb. 19, 2015.*
(Continued)

*Primary Examiner* — Christopher Adam Hixson
(74) *Attorney, Agent, or Firm* — Marshall, Gerstein & Borun LLP (57) ABSTRACT

A sorting chamber (1) for sorting first particles (25) from second particles (26) comprising: an internal chamber (7), which is delimited by a base wall (2), a top wall (4), and a spacer (6), set between the base wall (2) and the top wall (4); an internal chamber (7), which is at least partially-delimited by the base wall (2) and top wall (4); two passages (8), which set in communication the internal chamber (7) with the external environment; and a plurality of cavities (9), which are designed to house the first particles (25), are made in the base wall (2) and have openings (10) towards the internal chamber (7) with widths of from 4 to 6 μm.

24 Claims, 10 Drawing Sheets (51) Int. Cl.
 C12M 1/00 (2006.01)
 G01N 15/02 (2006.01)
(52) U.S. Cl.
 CPC ............... *B01L 2200/0652* (2013.01); *B01L 2300/0816* (2013.01); *B01L 2300/0851* (2013.01); *B01L 2400/0409* (2013.01); *C12M 47/04* (2013.01); *G01N 2015/0288* (2013.01)
(58) Field of Classification Search
 CPC ..... B01L 2300/0816; B01L 2300/0851; B01L 2400/0409; C12M 47/04; C12N 1/4077; G01N 2015/0288; G01N 1/34; G01N 2015/0019; G01N 15/02; G01N 2015/0065; G01N 2015/0073; G01N 2015/008; G01N 2015/0084; Y10T 436/25375
 See application file for complete search history.

(56) References Cited

U.S. PATENT DOCUMENTS

2005/0211557 A1    9/2005  Childers et al.
2007/0160503 A1*   7/2007  Sethu ................ A61M 1/3633
                                              422/400

OTHER PUBLICATIONS

Lassner, Dirk et al. "Cell Sorting System for the Size-Based Sorting or Separation of Cells Suspended in a Flowing Liquid." Translation of WO 2003/56330 A2 by FLS, Inc., Oct. 2015.*
International Search Report in international application No. PCT/IB2009/007010, dated Jan. 8, 2010.

* cited by examiner

SORTING CHAMBER FOR MICROSCALE PARTICLES

CROSS-REFERENCE TO RELATED APPLICATIONS

This is the U.S. national phase application of International Application No. PCT/IB2009/007010, filed Oct. 1, 2009, which claims the benefit of Italian Patent Application No. BO2008A 000602, filed Oct. 2, 2008.

TECHNICAL FIELD

The present invention relates to a sorting chamber, a sorting device, and uses of a sorting chamber and/or device.

STATE OF THE ART

The devices that have been up to now proposed for sorting particles, in particular, cells, envisage passing a flow, which contains the sample on which sorting is to be carried out, at pressure through a filtering apparatus that removes the cells of larger size from the cells of smaller size.

Examples of this type of devices are described in the patent applications Nos. WO2006108101, WO2005047529, and in P. Sethu, A. Sin, M. Toner; Microfluidic diffusive filter for apheresis (leukapheresis); Lab Chip, 2006, 6, 83-86.

Known devices of the type described above have the disadvantages of being relatively complex and costly and of treating the sample at a relatively high pressure (sorting, in practice, is carried out by exploiting the pressure to which the flow is subjected). The relatively high pressure can damage the cells and calls for equipment that is sufficiently resistant and relatively complex. Where these devices were to be used at low pressure, the operations of sorting would be very slow and almost unfeasable.

The patent application having publication No. WO03/056330 describes a device for sorting cells of different sizes. This document does not, however, in any way take into consideration the possibility of sorting erythrocytes from leukocytes and of making a device for this purpose. In particular, WO03/056330 describes the use of a device on a sample without erythrocytes (see, for example, page 16, lines 5 and 6, and page 20, lines 27-32).

The U.S. Pat. No. 6,190,919 describes a device for improving the deglycerolization of red blood cells. Hence, nor does this document in any way take into consideration the possibility of sorting erythrocytes from leukocytes and of making a device for this purpose. The device described in U.S. Pat. No. 6,190,919 has a plurality of channels (designated in the text and in the figures with the reference numbers 42, 40, 38, 36, 34, 32 and 31), through which there flows a solution containing particles; it does not, instead, have cavities, in which material can be housed and collected.

SUMMARY

The aim of the present invention is to provide a sorting chamber, a sorting device, and uses of a sorting chamber and/or a device, that will enable the drawbacks of the state of the art to be overcome at least partially and will, at the same time, be easy and inexpensive to produce.

According to the present invention a sorting chamber, a sorting device, and uses of said sorting chamber and/or a device are provided according to what is recited in the ensuing independent claims and, preferably, in any one of the claims directly or indirectly dependent thereon.

BRIEF DESCRIPTION OF THE DRAWINGS

The invention is described hereinafter with reference to the annexed drawings, which illustrate some non-limiting examples of embodiment thereof and in which.

EMBODIMENTS OF THE INVENTION

Figure 1:
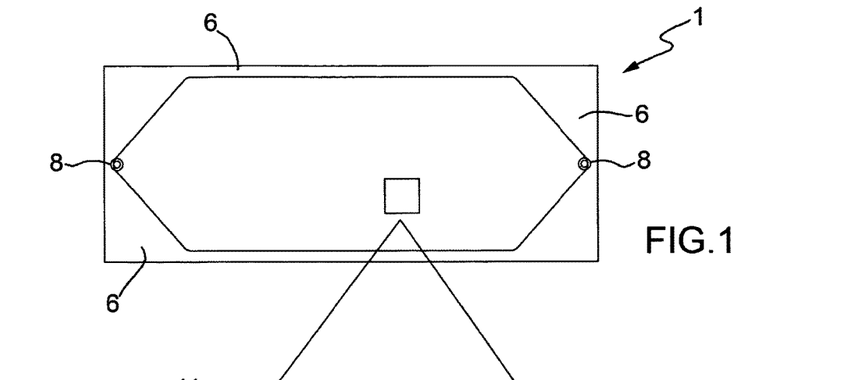
FIG. 1 is a top plan view of a sorting chamber in accordance with the present invention.
Figure 2:
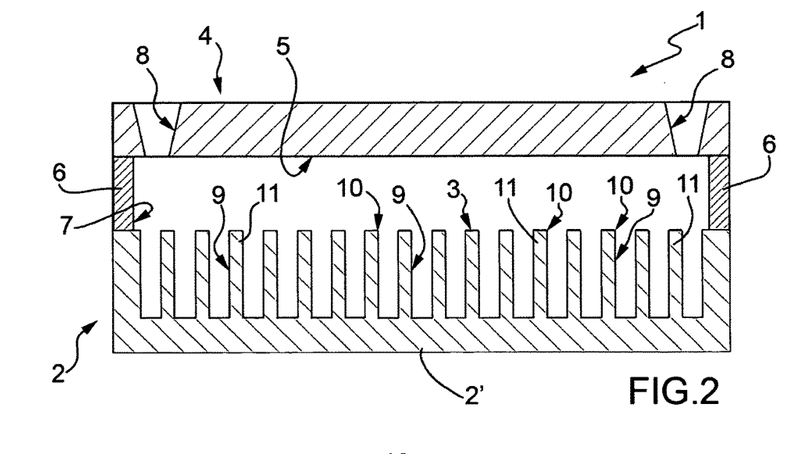
FIG. 2 is a cross-sectional and schematic view of the chamber of FIG. 1.

In FIGS. 1 and 2, designated as a whole by 1 is a sorting chamber, which can advantageously be used for sorting particles of different sizes of an organic sample (substantially liquid, in particular, an aqueous solution). In particular, the chamber 1 can be used for sorting particles of a first type from particles of a second type, where the particles of the first type have at least one dimension larger than the dimensions of the particles of the second type.

In the present text, by "particle" is meant a corpuscle having the major dimension smaller than 1000 µm (advantageously smaller than 260 µm). Non-limiting examples of particles are: cells, cellular detritus (in particular, cell fragments), cell aggregates (such, as, for example, small clusters of cells deriving from stem cells, such as neurospheres or mammospheres), bacteria, lipospheres, (polystyrene and/or magnetic) microspheres, complex nanospheres (for example, nanospheres of up to 100 nm) formed by microspheres bound to cells. According to some embodiments, the particles are chosen in the group consisting of: cells and cellular detritus. Advantageously, the particles are cells.

According to some embodiments, the particles (advantageously cells and/or cellular detritus) have the major dimension smaller than 60 µm.

In the present text, by "dimensions of a particle" is meant the length, the width, and the thickness of the particle.

By way of example, it is emphasized that an erythrocyte has an average length and an average width of approximately 8 μm and an average thickness of approximately 3 μm; a leukocyte has an average length, an average width, and an average thickness of approximately 9-12 μm (in other words, the leukocyte may be considered to a first approximation almost spherical). In this case, in other words, the erythrocyte has at least one dimension (in particular, the thickness) smaller than the dimensions (length, width, and thickness) of the leukocyte.

As further example, it should be recalled that a spermatozoon has a head having an average length of approximately 6-10 μm, an average width, and an average thickness of approximately 3-5 μm; an epithelial cell has dimensions in the region of 50 μm. In this case, in other words, the spermatozoon has at least one dimension (in particular, the width and the thickness) smaller than the dimensions (length, width, and thickness) of the epithelial cell.

As further examples, it should be recalled that both the platelets and the cellular detritus have dimensions smaller than those of both erythrocytes and leukocytes; the clusters have dimensions larger than those of both erythrocytes and leukocytes.

Typically, the chamber 1 has a length of approximately 50 mm, a width of approximately 20 mm and a thickness of approximately 1.2 mm.

The chamber 1 comprises a base wall 2, which has an inner surface 3, a top wall 4 (lid), which has an inner surface 5 substantially facing the surface 3, and a spacer element 6, which is set between the walls 2 and 4 for connecting the walls 2 and 4 themselves in a fluid-tight way so as to keep the surfaces 3 and 5 at a distance from one another. The walls 2 and 4 are substantially parallel and face one another. The spacer element 6 extends substantially along the entire perimeter of the walls 2 and 4.

The walls 2 and 4 and the spacer element 6 delimit an internal chamber 7. In particular, the spacer element 6 delimits the chamber 7 laterally, and the walls 2 and 4 delimit the chamber 7 at the bottom and at the top, respectively.

The wall 4 has two passages 8 (in particular, two holes), which are designed to set in contact the chamber 7 with the external environment and have a preferably shape (in particular, that of a truncated cone) tapered inwards. Typically, each passage 8 has a major diameter (facing the outside) of approximately 1200 μm, and a minor diameter (facing the chamber 7) of approximately 700 μm.

Note that the chamber 7 is set in communication with the external environment only through the passages 8, which are sized in such a way as not to allow passage of an aqueous solution as a result of just the force of gravity.

According to an alternative embodiment (not illustrated), the wall 4 is without the passages 8 and/or holes, which are, instead, provided through the spacer element 6.

According to an alternative embodiment (not illustrated), the wall 4 is without the passages 8 and/or holes, which are, instead, provided through the wall 2.

According to further embodiments (not illustrated), the passages 8 are more than two.

Figure 3:
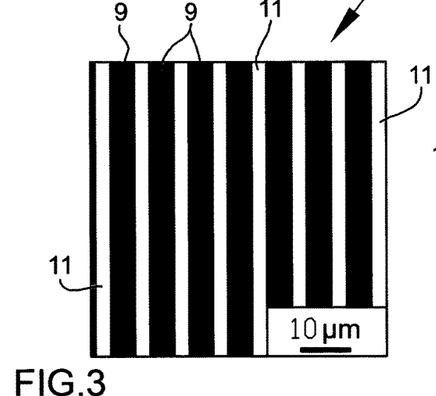
FIG. 3, illustrates a detail of FIG. 1 at an enlarged scale.

With particular reference to FIGS. 2 and 3, the wall 2 has a plurality of cavities 9, which are closed towards the outside (in particular, downwards) by a bottom portion 2' of the wall 2, and each have at least one respective opening 10 facing the chamber 7 (in particular, upwards). The cavities 9 are separated from one another by substantially linear internal walls 11 substantially parallel to one another. In FIG. 3, the cavities 9 are represented in grey/black, and the walls 11 are represented in white.

Each cavity 9 is closed at an end opposite to the respective opening 10.

Figure 7:
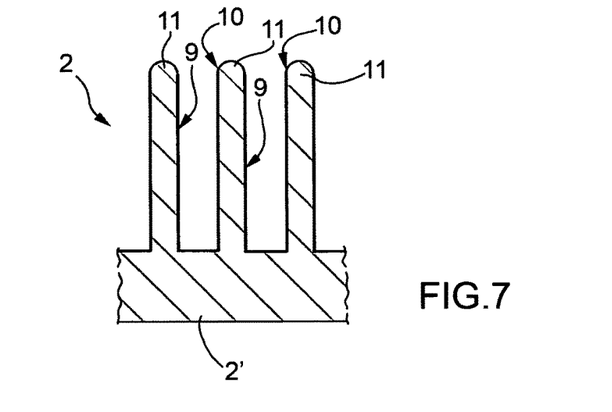
FIGS. 7 and 8 illustrate different embodiments of a detail of FIG. 2.
Figure 8:
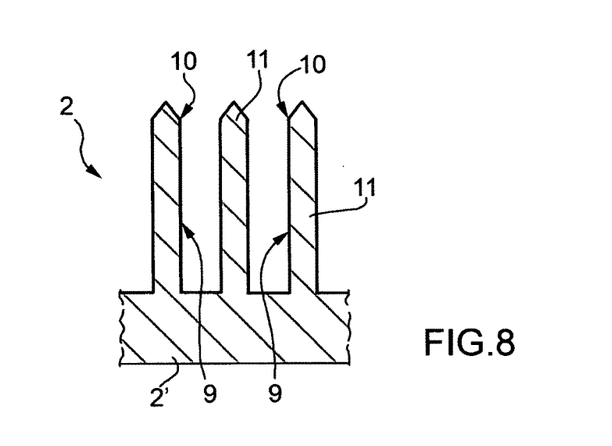
Figure 9:
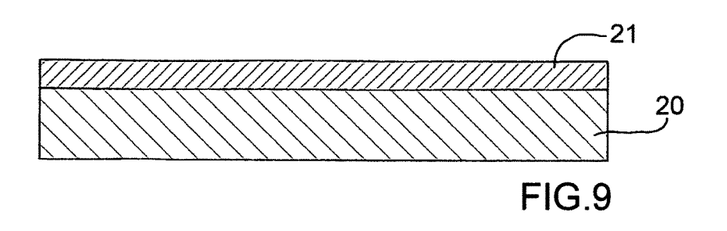
FIGS. 9 to 16 illustrate, in cross-sectional view, successive steps of a method for the production of the chamber of FIG. 2.
Figure 10:
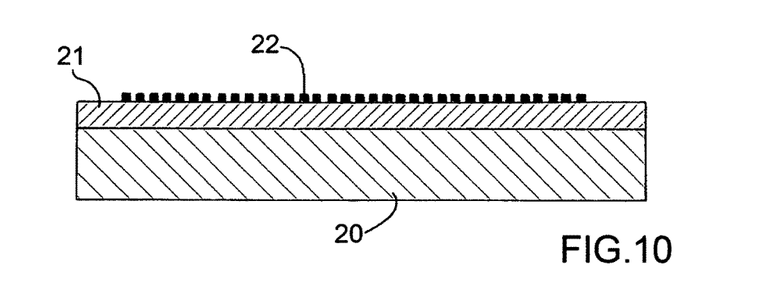

FIGS. 7 and 8 illustrate further different embodiments of the walls 11. In the variant of FIG. 7, the walls 11 have respective rounded top ends. In the variant of FIG. 8, the walls 11 have respective top ends shaped like a V set upside down.

Each cavity 9 is shaped so as to receive and house a plurality of cells of smaller dimensions (for example, erythrocytes or spermatozoa), and so that it is not possible for cells of larger dimensions (for example, leukocytes or epithelial cells) to gain access.

In particular, each opening 10 has a width smaller than the dimensions of the cells of the second type and larger than the minor dimension of the cells of the first type; each opening 10 (in particular, also each cavity 9) has a length larger than the major dimension of the cells of the first type.

In the present text, by "width of the opening" 10 is meant the maximum diameter of a sphere that is able to pass through the opening 10. In the present text, by "length of the opening" 10 is meant the major dimension of the opening 10 itself.

In this regard, note that, in the embodiment illustrated in FIGS. 2 and 3, the width of each opening 10 corresponds to the distance between two adjacent walls 11. In this case, the length of each opening 10 is the dimension of the opening 10 itself substantially perpendicular to the width.

Figure 5:
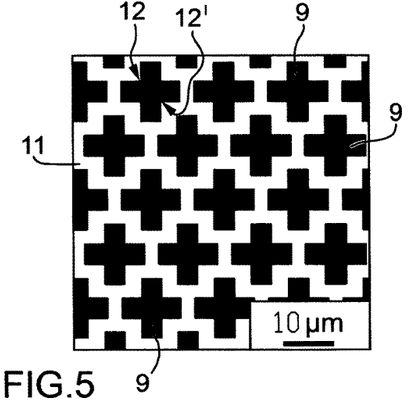

FIG. 5 illustrates an alternative embodiment in which the wall 2 comprises a plurality of cavities 9 (represented in grey/black) substantially in the form of a cross and delimited by a wall 11 shaped for this purpose. In this specific case, the width of an opening 10 corresponds to the distance between the sharp edges designated by the numbers 12 and 12'. In this case, the length of each opening 10 is the dimension of the opening 10 itself substantially at 45° to the width.

Figure 4:
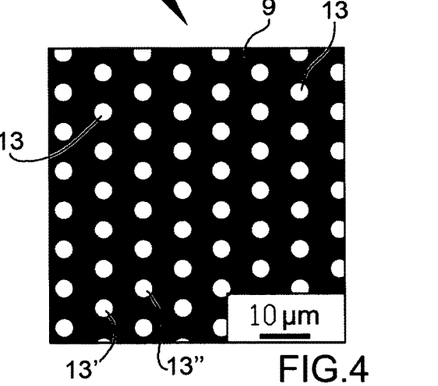
FIGS. 4 to 6 illustrate different embodiments of the detail of FIG. 3.

FIG. 4 illustrates an alternative embodiment, in which the part 2 comprises a cavity 9 (represented in grey/black) and a plurality of substantially cylindrical column elements 13 that project from the bottom portion 2' towards the wall 4. The column elements 13 are arranged in rows and columns in staggered order. In this specific case, the width of the opening 10 corresponds to the distance between the column elements 13' and 13", which are in adjacent rows and columns.

Figure 6:
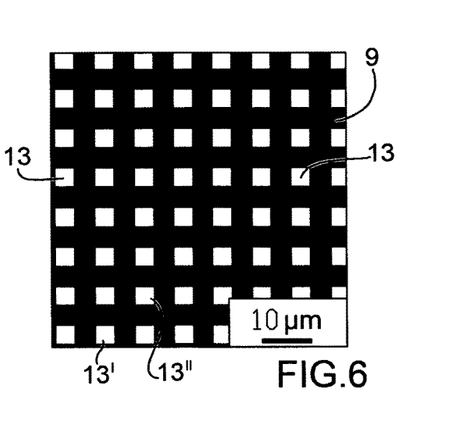

FIG. 6 illustrates an alternative embodiment, in which the part 2 comprises a cavity 9 (represented in grey/black) and a plurality of column elements 13 with square cross section, which project from the bottom portion 2' towards the wall 4, arranged in an array of rows and columns. In this specific case, the width of the opening 10 corresponds to the distance between the facing sharp edges of the column elements 13' and 13", which are not in the same row and same column, but in adjacent rows and columns.

According to alternative embodiments, the wall 2 is structured in such a way as to have a plurality of cavities 9 shaped like the parts represented in white in FIG. 4 and/or FIG. 6. According to an alternative embodiment, the wall 2 is structured in such a way as to have a cavity 9 shaped like the part represented in white in FIG. 5.

The walls 11 and/or the column elements 13 function as delimiting elements; namely, they delimit the cavities 9 at least partially.

The width of the opening/s 10 is generally smaller than 250 μm.

Advantageously, each opening 10 has a width of less than 40 μm. According to some embodiments, each opening 10 has a width of less than 22 μm, in particular, from 20 μm to 100 nm.

Advantageously, each opening 10 has a width of less than 8 μm. According to some embodiments, each opening 10 has a width of from 3 to 8 μm. Advantageously, each opening 10 has a width of from 4 to 6 μm, in particular, from 4 to 5 μm. According to specific embodiments, each opening 10 has a width of approximately 5 μm. These widths are particularly useful, for example, in the case where the aim is to sort erythrocytes from leukocytes, or spermatozoa from epithelial cells.

Advantageously, each opening 10 has a width of less than 3 μm. According to some embodiments, each opening 10 has a width of less than 1 μm. Advantageously, each opening 10 has a width of from 1 μm to 100 nm, in particular, from 0.5 μm to 150 nm. These widths are particularly useful, for example, in the case where the aim is to sort cellular detritus from a cellular suspension (namely, cells contained in a solution).

According to some embodiments, each opening 10 has a length of at least 9 μm. Advantageously, each opening 10 has a length of at least 11 μm.

According to some embodiments, each cavity 9 has a length of at least 9 μm. Advantageously each cavity 9 has a length of at least 11 μm.

According to some embodiments, each cavity 9 has a depth of at least 1 μm, advantageously at least 3 μm. These depths are particularly useful, for example, in the case where the aim is to sort cellular detritus or platelets from other cells (for example, leukocytes and/or erythrocytes).

To trap particles of a substantially spherical shape the depth of the cavity is substantially more than half the width, advantageously larger than the width. To trap particles of non-spherical shape (such as, for example, erythrocytes) advantageously each cavity 9 has a depth at least twice its own width.

According to some embodiments, each cavity 9 has a depth of at least 10 μm. Advantageously, each cavity 9 has a depth of from 10 μm to 50 μm. According to specific embodiments, each cavity 9 has a depth of approximately 20 μm. These depths are particularly useful, for example, in the case where the aim is to sort erythrocytes from leukocytes, or spermatozoa from epithelial cells.

According to some embodiments, each cavity 9 has a depth of at least 250 μm. Advantageously, each cavity 9 has a depth of at least 50 μm. These depths are particularly useful, for example, for sorting small aggregates of stem cells (such as, for example, neurospheres or mammospheres) from a cellular suspension.

The delimiting elements (namely, the walls 11 and/or the column elements 13) are set at a distance from the wall 4. In particular, according to some advantageous embodiments, the distance between the delimiting elements and the wall 4 is from 10 to 500 μm.

According to some embodiments, the delimiting elements (or element) have (has) a width of at least 1 μm. According to some embodiments, the delimiting elements (or element) have (has) a width of up to 5 μm. In particular, the delimiting elements (or element) have (has) a width of from 1 to 5 μm.

Advantageously, the delimiting elements (or element) have a width of up to 3 μm. In particular, the delimiting elements (or element), have (has) a width of from 1 to 3 μm. Typically, the delimiting elements (or element) have a width of 3 μm.

It has been surprisingly found experimentally that these dimensions of the delimiting elements or element in combination with the dimensions of the cavity or cavities 9 enables a sorting of the erythrocytes from the leukocytes that is particularly effective and delicate.

The various dimensions indicated in this text (for example, the dimensions of the particles and/or of the openings and/or of the delimiting elements) can be measured with microscopes with graduated scale or with normal microscopes used with slides.

According to a further aspect of the present invention, a sorting device 14 is provided, equipped with a sorting chamber 1, which in turn comprises: a base wall 2, which has an inner surface 3; a top wall 4, which has an inner surface 5 and is connected in a fluid-tight way with the wall 2; an internal chamber 7, which is at least partially delimited by the walls 2 and 4; at least one passage 8, which sets the chamber 7 in communication with the outside world; and at least one cavity 9, which has at least one opening 10 towards the internal chamber 7 and is closed towards the outside world. Advantageously, the chamber 1 has the geometrical and dimensional characteristics defined above without reference to the particles of the first and/or second type (i.e., without reference to the dimensions of the particles themselves).

Figure 18:
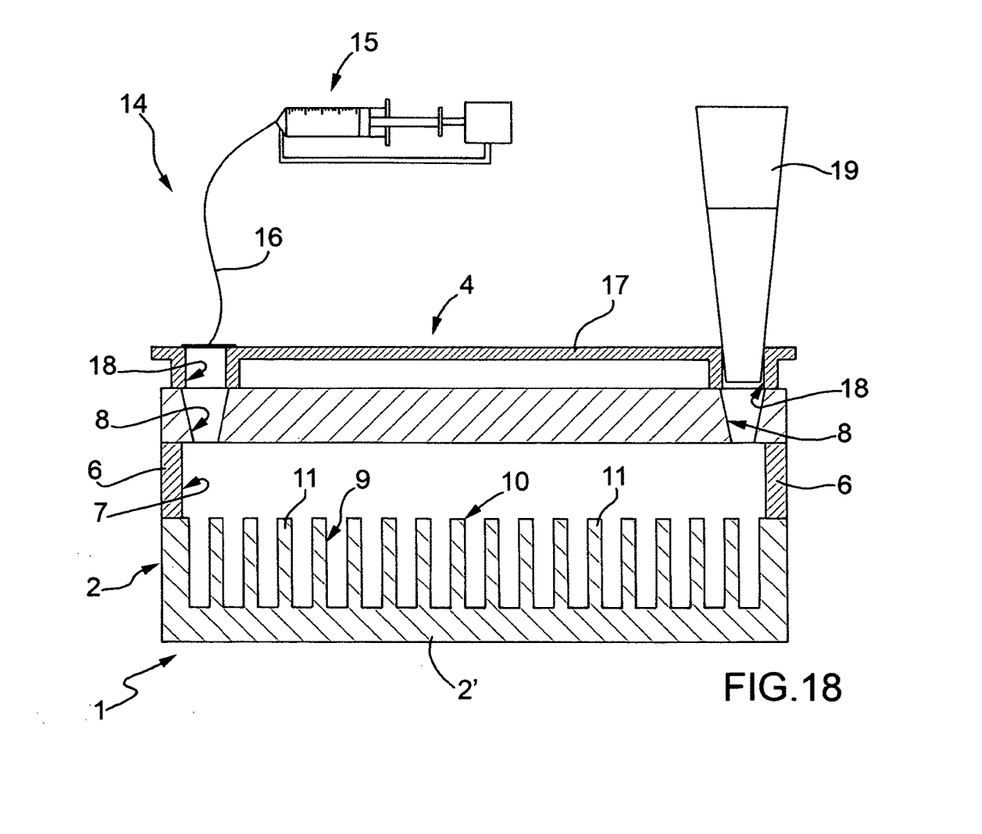
FIG. 18 illustrates, in cross-sectional view, a sorting device in accordance with the present invention.

With particular reference to FIG. 18, according to some embodiments, the device 14 moreover includes a pumping unit 15, in particular, comprising a syringe with numeric-control actuator, the syringe being connected to the chamber 1 by means of a duct 16.

The device 14 moreover comprises a gasket 17 (preferably made of elastomeric material) equipped with a number of holes 18 for connecting the duct 16 and possibly a reservoir 19 (for example, the tip of a pipette) to the chamber 1.

According to some embodiments, the reservoir 19 is part of the device 14.

With particular reference to FIGS. 9 to 16, described hereinafter is a methodology provided by way of non-limiting example for producing the chambers 1 described above.

On top of a silicon layer 20 (FIG. 9) a layer 21 of photopolymerizable material (for example, SU8, or else one containing PMMA) was applied; the application was performed by means of a known technique chosen from among: lamination, spin- or spray-coating, chemical vapour deposition (CDV), physical vapour deposition (PVD).

A mask 22 was set (FIG. 10) on the layer 21, which was then irradiated from above with UV light so that only the exposed portions of the layer 21 were polymerized.

Alternatively, it is possible to use a lens and a pattern (of the negative of the etch that it is desired to obtain) at an enlarged scale positioned between a UV source and the layer 21.

Figure 11:
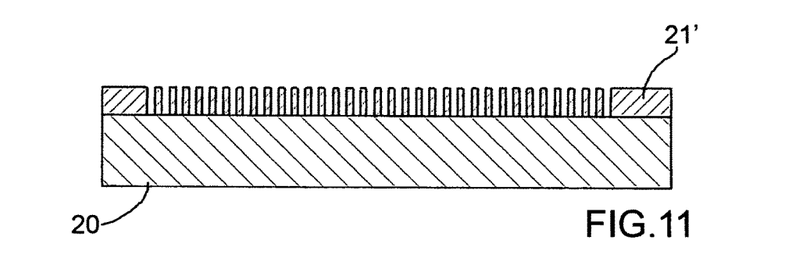
Figure 12:
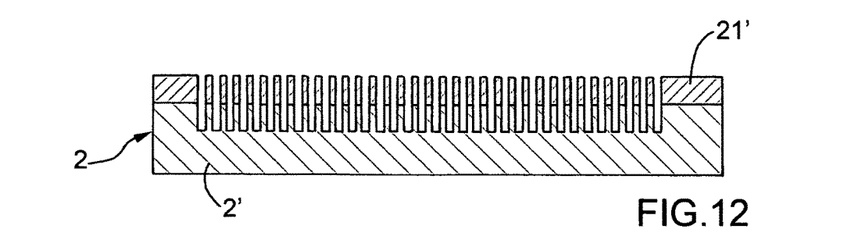
Figure 13:
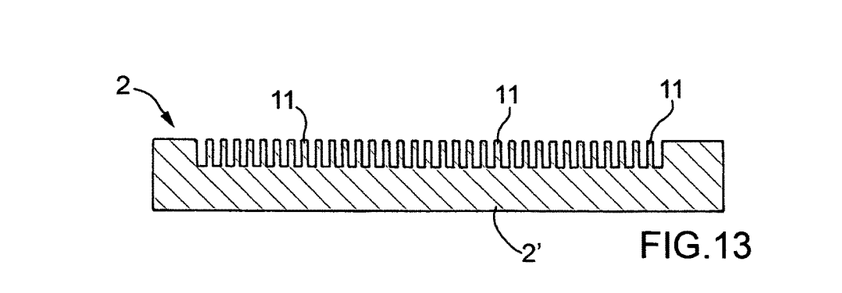
Figure 14:
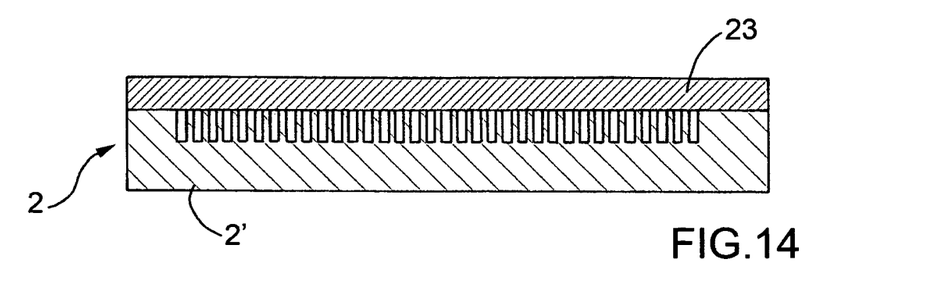
Figure 15:
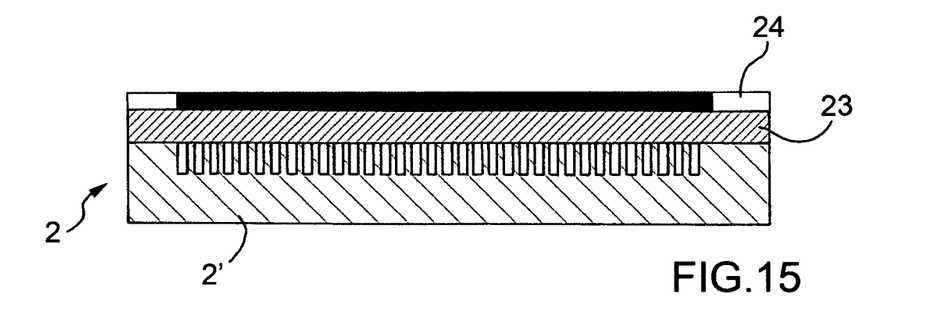
Figure 16:
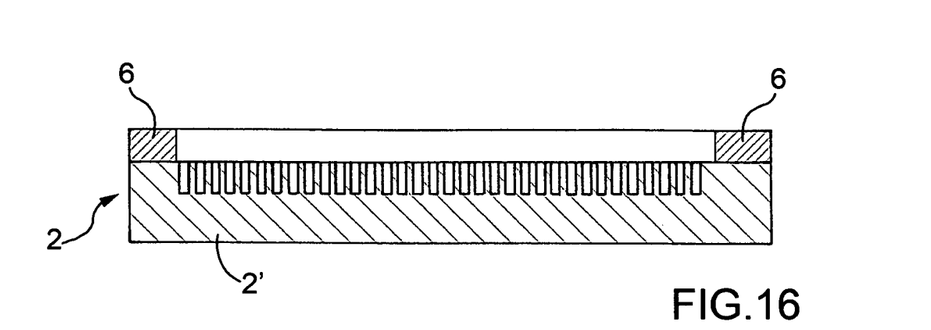

Once polymerization has been carried out selectively, the non-polymerized material was removed (FIG. 11). At this point (FIG. 12), the layer 20 was etched using DRIE (Deep Reactive Ion Etching) [this etching methodology and alternative methodologies to obtain the chamber 1 are described in O. Geschke, H. Klank, P. Telleman (Eds.) "Microsystem Engineering of Lab-on-a-chip devices" (second edition) ISBN: 978-3-527-31942-8, Wiley-VCH 2008; Marc. J. Madou, "Fundamentals of Microfabrication, the Science of Miniaturisation", (second edition) CRR, ISBN: 0849308267, the contents of which are recalled integrally herein for reasons of completeness of description]. The polymer (layer 21') was then removed (FIG. 13) using phosphoric acid and hydrogen peroxide (solution known as piraña) so as to obtain the wall 2.

Deposited by means of lamination on the wall 2 (FIG. 14) was a Dry Resist® layer 23 (in particular, Ordyl SY300—Elga Europe). At this point, a mask 24 (for example, a printed transparency or a selectively chrome-plated glass) (FIG. 15) was positioned on the layer 23, which has been irradiated with UV light.

The non-solidified Dry Resist® was removed with a solvent (for example, BMR developer, which is a xylene-based mixture with butoxy-ethyl acetate) (FIG. 16), so as to obtain the spacer element 6.

At this point, the wall 4 (generally made of glass) was connected in a fluid-tight way to the spacer 6 by applying pressure and/or heat so as to obtain the chamber 1 illustrated in FIGS. 1 and 2.

According to other processes, the chamber 1 could be made of thermoplastic polymer by means of "hot embossing". In this case, a mould is obtained that reproduces the negative of the wall 2 and of the spacer 6 in a single piece, which is hot-pressed on a plate of thermoplastic polymer for impressing the shape, on which there is then applied, by hot-gluing or using processes assisted by solvents or adhesives, the top wall 4 made of glass (obtained using technologies similar to the ones described previously) or polymer (obtained via laser-etching, hot-embossing, injection-moulding, milling, etc.)

According to other processes, the chamber 1 can be made of polymeric material by means of injection-moulding. In this case, the wall 2 and the spacer 6 are made of a single piece by extruding the hot molten polymer into a closed mould. The top wall 4 is made and glued, as in the process described previously.

According to other processes, the chamber 1 can be made of polymeric material by means of casting. In this case, the wall 2 and the spacer 6 are made of a single piece by pouring the polymer in polymerization phase into an open mould. The top wall 4 is made and glued as in the process described previously.

According to other processes, the chamber 1 can be subjected to surface anti-adherent treatments (PEG or fluorinated polymers) to reduce the adherence of the particles.

According to a further aspect of the present invention, there is provided a use of a chamber 1, as described above (or else a device 14 as described above) for sorting particles (in particular, cells) of a first type from particles (in particular, cells) of a second type, where the particles of the first type have at least one dimension larger than the dimensions of the particles of the second type.

According to some embodiments, the particles of the first type are erythrocytes and the particles of the second type are leukocytes.

According to alternative embodiments, the particles of the first type are spermatozoa and the particles of the second type are epithelial cells.

According to some embodiments, the particles of the first type are cellular detritus and the particles of the second type are cells.

Advantageously, the use comprises an insertion step, during which a sample is inserted into the chamber 1; a movement step, during which a relative reciprocating motion (advantageously horizontal) is induced between the chamber 1 and the sample (advantageously by stirring the fluid); and a sample-taking step, during which a part of the sample is taken. The sample-taking step is subsequent to the movement step.

According to some embodiments, the reciprocating motion is obtained by shaking the chamber and/or by exerting a slight negative pressure alternately to a positive pressure on the sample.

Note that in use, once the sample has been inserted, the particles of the first type by the force of gravity drop into the cavity/cavities 9 whilst the particles of the second type remain in the chamber 7 on top of the cavity/cavities 9. When the part of the sample is removed from the chamber 1, the large majority of the particles of the first type remain "trapped" in the cavity/cavities 9, whilst almost all of the particles of the second type are removed together with the aforementioned part of the sample.

The fact of exploiting the force of gravity and, hence, not applying a pressure for sorting the particles of the first type from the particles of the second type determines important advantages as compared to the state of the art, amongst which there may be cited: simplicity and economy (also the materials do not have to be such as to withstand high pressures) of the chamber 1, reduction of the risk of damage to the cells during sorting, better sorting of the cells of the first type from the cells of the second type, and possible use of the chamber 1 as a disposable element, with consequent reduction of the risks of contamination.

The use described above can advantageously be applied when there is an interest in recovering the particles of the second type. Examples, in this regard, are: sorting of erythrocytes from leukocytes (the latter are usually the cells of effective interest); sorting of cellular detritus from cell matrices (the latter usually being of effective interest).

In particular, the use described above can be adopted for sorting: lymphocytes from erythrocytes, and/or detritus and/or platelets; particles of larger dimensions (as compared to detritus) from detritus; particles of larger dimensions (as compared to bacteria) from bacteria; stem cells, such as neurospheres or mammospheres, from other particles of smaller dimensions (as compared to the stem cells); lipospheres from other particles of smaller dimensions; oocytes from other particles of smaller dimensions (as compared to the oocytes); polystyrene and/or magnetic microspheres (bound to cells) from cells.

According to some embodiments, the use comprises a centrifuging step, which is subsequent to the sample-taking step and during which the chamber 1 undergoes centrifugation so that the particles of the first type come out of the cavity/cavities 9; a recovery step, which is subsequent to the centrifuging step and during which a further part of the sample containing the particles of the first type is taken from the chamber 1.

This type of use can be advantageously exploited when there is interest in recovering the particles of the first type. An example, in this regard, is the sorting of spermatozoa from epithelial cells. Further examples are sorting of: cells from clusters; and cells from polystyrene and/or magnetic microspheres (bound to cells).

This type of use can also be advantageously exploited when there is interest in recovering both particles of the first type and particles of the second type. An example, in this regard, is the sorting of cells bound to functionalized microspheres from a suspension of cells.

According to some embodiments, the sample-taking step (or the recovery step) envisages recovery of the part (or the further part) of the sample within the reservoir 19.

According to alternative embodiments, when at least one of the passages 8 is provided through the wall 2 (FIG. 26) and not through the wall 4, after the centrifuging step, the chamber 1 is held so that the wall 2 is oriented upwards (namely, in such a way that the wall 2 is on top of the wall 4). In this way, there is a reduction in the risk, prior to or during the recovery step, of particles of the second type dropping into the cavity/cavities 9.

Figure 26:
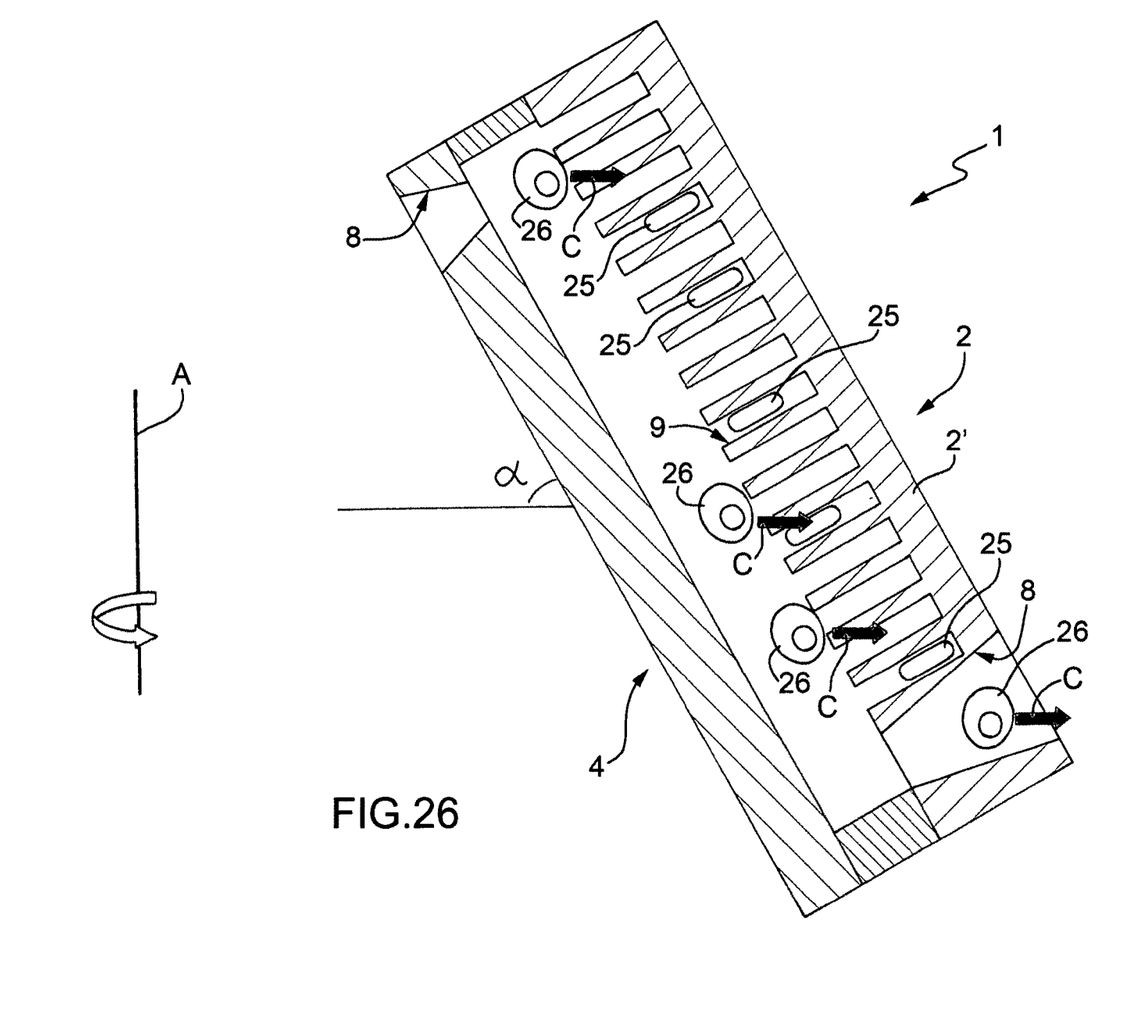
FIG. 26 is a cross-sectional and schematic view of a further embodiment of a chamber built in accordance with the present invention, during a step of use.

When the chamber 1 has the structure illustrated in FIG. 26, it is possible to perform the sample-taking step by tilting the chamber 1 by an angle α and by turning the chamber 1 itself about an axis A (the arrows C indicate the direction of the centrifugal force that is consequently applied to what is set between the walls 11 and the wall 4, in the case in point, to the leukocytes 26). In this way, the part of the sample to be taken (in the example illustrated, containing the leukocytes 26) flows through the passage 8 provided through the wall 2.

According to alternative embodiments, when at least one of the passages 8 is provided through the spacer element 6 and not through the wall 4, it is possible to recover the part (or the further part) of the sample by means of centrifugation of the chamber 1 or else by tilting the chamber 1 itself so as to orient at least one passage 8 downwards.

Figure 27:
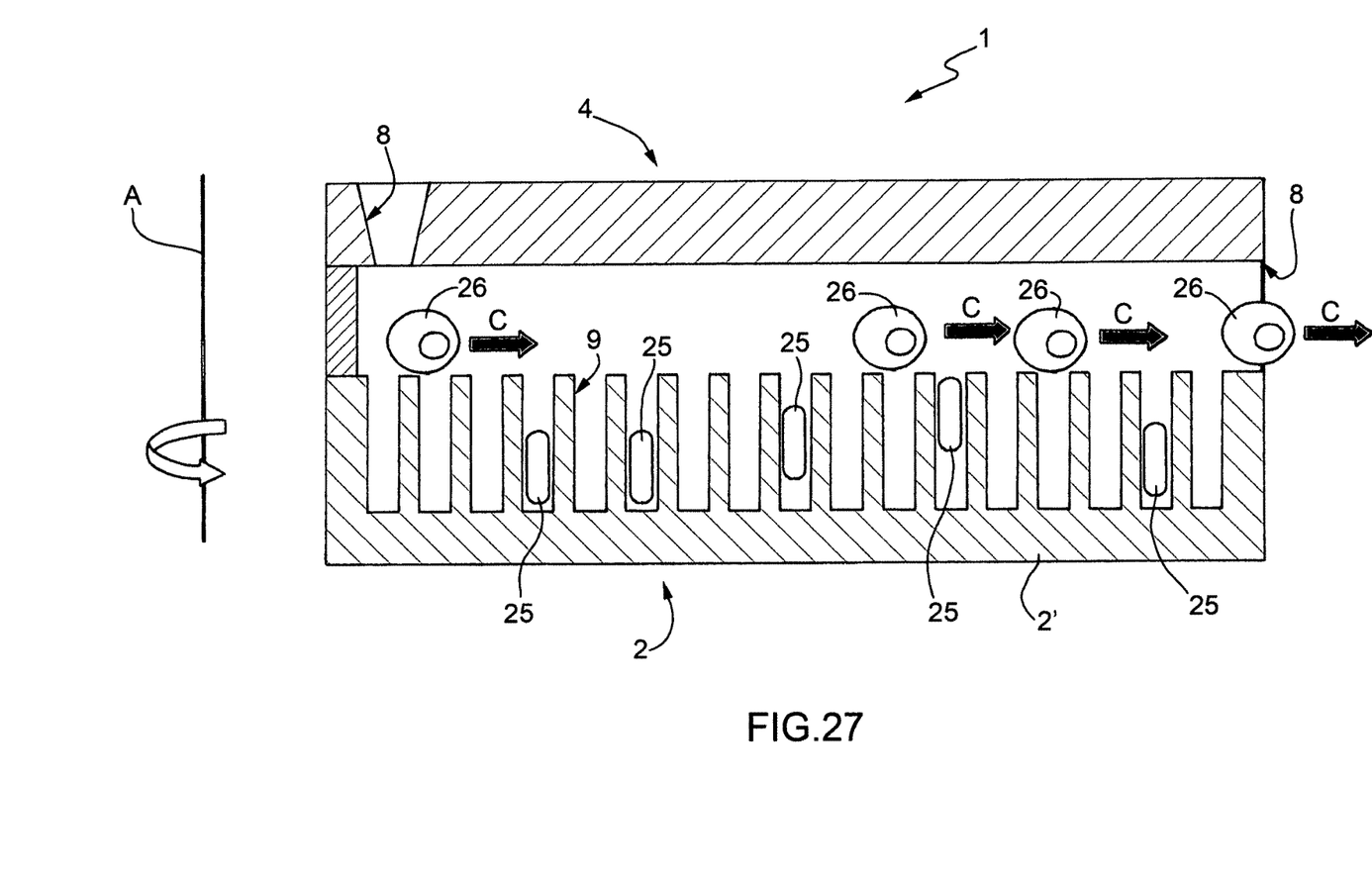
FIG. 27 is a cross-sectional and schematic view of a further embodiment of a chamber made in accordance with the present invention, during a step of use.

When the chamber 1 has the structure illustrated in FIG. 27, it is possible to perform the sample-taking step by keeping the chamber 1 substantially flat and by turning the chamber 1 itself about an axis A (the arrows C indicate the direction of the centrifugal force that is consequently applied to what is set between the walls 11 and the wall 4, in the case in point, to the leukocytes 26). In this way, the part of the sample to be taken (in the example illustrated, containing the leukocytes 26) flows through the passage 8 provided through the spacer 6.

Unless otherwise explicitly indicated, the contents of the references (articles, texts, patent applications, etc.) cited in this text are integrally recalled herein for reasons of completeness of description. In particular, the aforementioned references are incorporated herein by reference.

The present patent application claims the priority of an Italian patent application (specifically, No. BO2008A000602), the contents of which are integrally recalled herein. In particular, the aforementioned Italian patent application is incorporated herein by reference.

Further characteristics of the present invention will emerge from the ensuing description of some merely illustrative and non-limiting examples of the use of the device 14 and of the chamber 1.

Example 1

Figure 17:
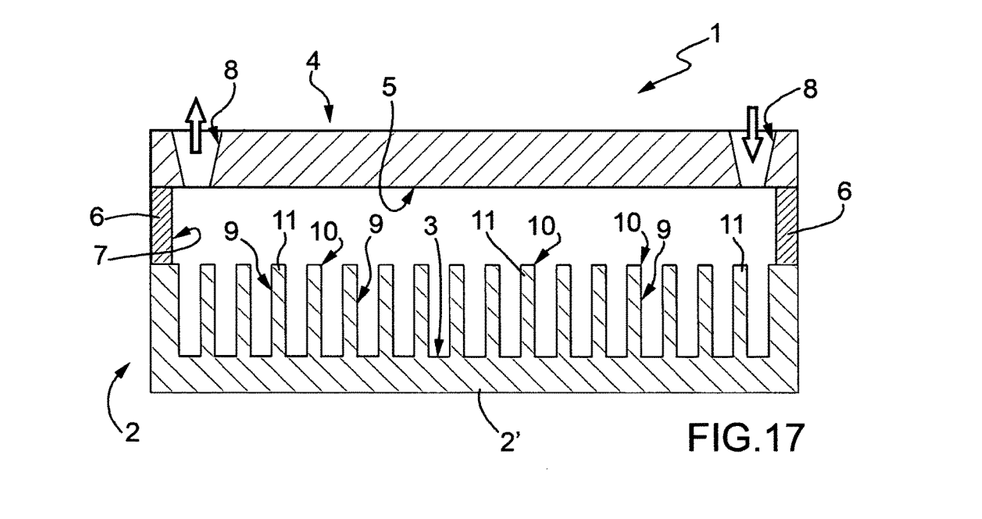
FIGS. 17, 19 and 20 illustrate, in cross-sectional view, different steps of a use of the chamber of FIG. 2 and of the device of FIG. 18.

In the device 14 illustrated in FIG. 18, there was first made to flow a solution of ethanol in water (70 wt % ethanol) and then a saline buffer (in particular, SPB—saline phosphate buffer) (approximately 5 ml) in the direction indicated by the arrows of FIG. 17 so as to fill in a substantially complete way the chamber 1 with the saline buffer itself. The chamber 1 used was as illustrated in FIGS. 1, 2 and 3 and presented the following dimensions:
internal volume: approximately 74 mm³
length: approximately 50 mm
width: approximately 20 mm
width of the cavities 9: approximately 5 µm
depth of the cavities 9: approximately 20 µm
width of walls 11: approximately 3 µm At this point, the reservoir 19 (in particular, a pipette) containing 40 µl of the sample (which contained concentrations of 150 000 erythrocytes/µl and 1500 leukocytes/µl) to be sorted was inserted into the gasket 17 and the sample itself was made to flow (100 µl/min) into the chamber 1 by operating the pumping unit 15 (FIG. 18).

Figure 19:
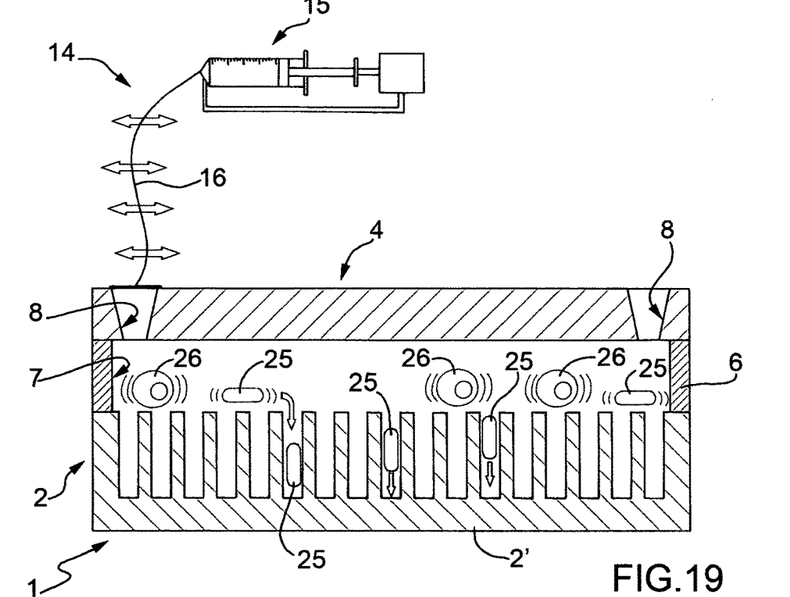

Next, the duct 16 was moved as indicated by the double-headed arrows appearing in FIG. 19 for some minutes (the times involved can possibly be considerably reduced if a vortex is used) so as to cause the chamber 1 to vibrate and allow the erythrocytes 25 to engage the cavities 9 whilst the leukocytes 26 remained on top of the cavities 9 themselves.

Figures 21, 22, 23:
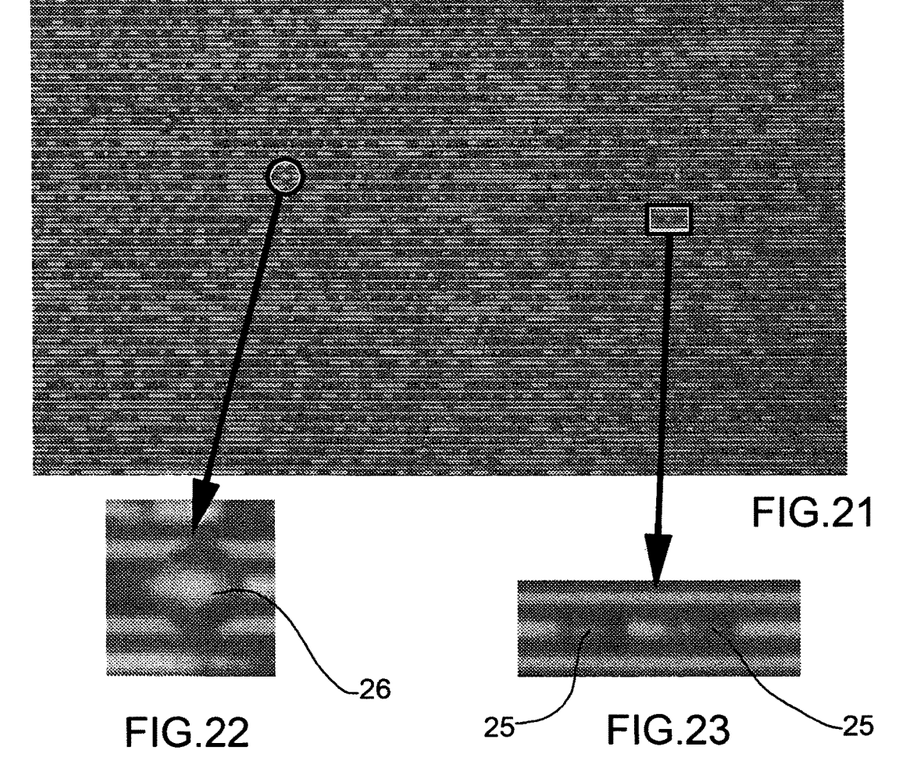
FIG. 21 is a photograph at an enlarged scale of a portion of the chamber of FIG. 2, in use.
FIGS. 22 and 23 are photographs of details of the photograph of FIG. 21 at an enlarged scale.

FIG. 21 is a photograph at an enlarged scale taken from above of a portion of the chamber 1 at the end of the vibrations. FIGS. 22 and 23 show, respectively, a leukocyte (set above the cavities 9) and two erythrocytes (arranged within a cavity 9).

Figure 24:
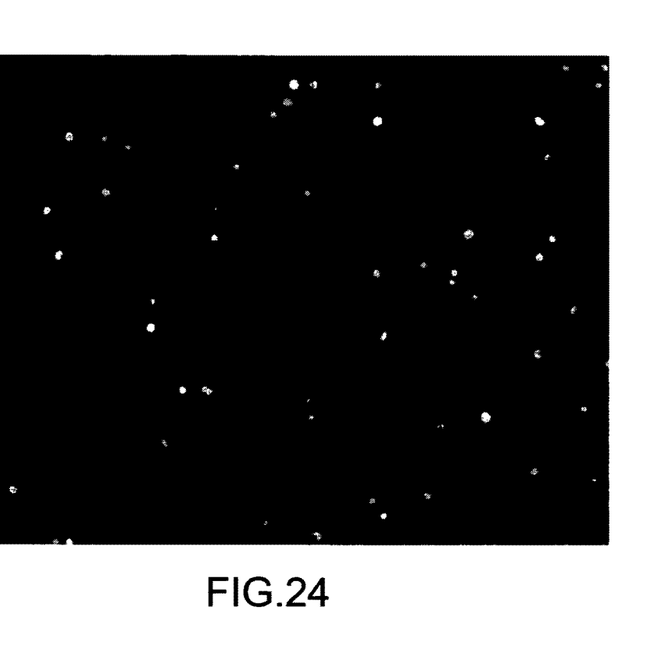
FIG. 24 is a photograph of the portion of FIG. 21, obtained using a DAPI filter (i.e., by irradiating with UV light and receiving in blue)
Figure 25:
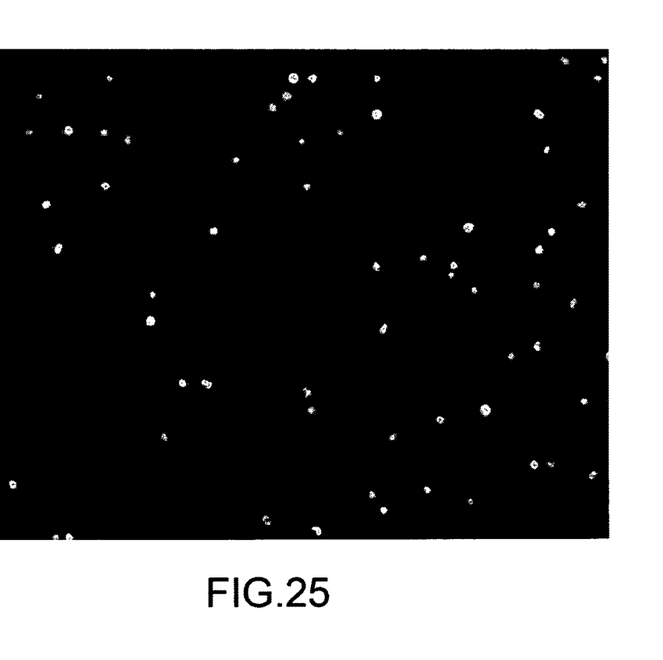
FIG. 25 is a superposition of the photographs of FIGS. 21 and 24.

FIG. 24 is a photograph of the same portion of the chamber 1 obtained with a DAPI filter (namely, by illuminating the sample with UV light and receiving in the blue). With said filter it is possible to highlight the nucleated cells (i.e., the leukocytes). FIG. 25 is a superimposition of the photographs of FIGS. 21 and 24.

Figure 20:
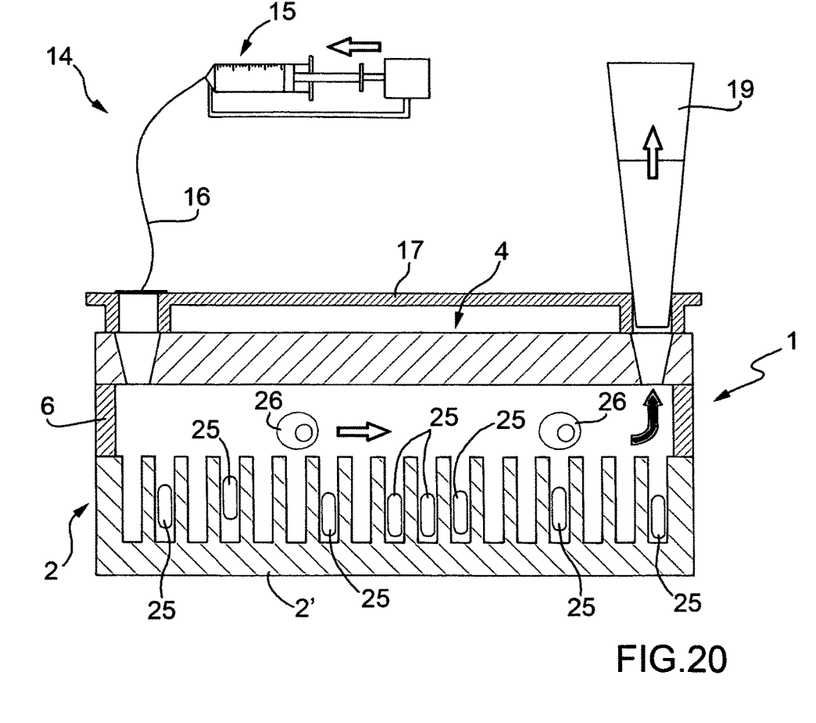

At this point, the sample was extracted from the chamber 1 (volume extracted: 200 µl; extraction flow: 40 µl/min) according to what is illustrated in FIG. 20. The sample extracted presented concentrations of 2500 erythrocytes/µl (elimination of 98.3%) and 1350 leukocytes/µl (recovery of 90%). Sorting proved to be extremely efficient.

Example 2

For sorting spermatozoa from epithelial cells the methodology described in Example 1 was adopted (obviously using a sample that contained said cells), at the end of which the chamber 1 (containing the buffer) was subjected to centrifugation so as to allow the spermatozoa to come out of the cavities 9. The centrifugation was performed by fixing the chamber 1 within a container that could be adapted to a commercial centrifuge. The chamber 1 was fixed in such a way as to remain perfectly vertical during rotation of the centrifuge and pressed on the side of the wall 4 against a gasket integrated in the container and designed to close the passages 8. In particular, the chamber 1 must be positioned in such a way that the centrifugal force has a direction perpendicular to the plane of the chamber 1 itself and sense oriented from the wall 2 to the wall 4. In this way, the centrifugal force favours pressing of the passages 8 on the gasket, not allowing the liquid to come out of the device and at the same time allowing the cells to come out of the cavities 9 and come to rest on the lid.

At this point, the saline buffer containing the spermatozoa was extracted from the chamber 1. The percentage of recovery of the spermatozoa was high.

The invention claimed is:

1. A sorting chamber for sorting particles of a first type from particles of a second type present within a sample; the particles of the first type being erythrocytes and having at least one dimension smaller than the dimensions of the particles of the second type, which are lymphocytes; the particles of the first type and of the second type having respective major dimensions smaller than 1000 µm;
the sorting chamber comprising:
a base wall, which has a first inner surface;
a top wall, which has a second inner surface and is connected in a fluid-tight way with the base wall;
an internal chamber, which is at least partially delimited by the base wall and top wall; and
at least one passage, which sets in communication the internal chamber with the external environment;
wherein the base wall comprises:
at least one cavity, which has at least one opening towards the internal chamber, and is closed at an end opposite the at least one opening such that the at least one cavity is closed towards the external environment, wherein the at least one cavity is adapted to receive and house at least one particle of the first type but not particles of the second type; and at least one wall or column that at least partially delimits the cavity and has a width of up to 5 µm;

said at least one opening having a width of from 3 µm to 8 µm.

2. The chamber according to claim 1, wherein the structure delimiting at least partially the cavity has a width of at least 1 µm.

3. The chamber according to claim 1, wherein said opening has a width of from 4 to 6 µm.

4. The sorting chamber according to claim 1, wherein said cavity has a depth of at least 10 µm.

5. The sorting chamber according to claim 1, wherein the cavity has a depth of from 10 µm to 50 µm.

6. The sorting chamber according to claim 1, wherein the cavity has a depth at least twice the width.

7. The sorting chamber according to claim 1, wherein the opening has a length of at least 9 µm.

8. The sorting chamber according to claim 1, wherein the cavity is sized to house a plurality of particles of the first type.

9. The sorting chamber according to claim 1, wherein the distance between the at least one structure delimiting at least partially the cavity and the second inner surface is from 10 to 300 µm.

10. The sorting chamber according claim 1, comprising a plurality of cavities.

11. The sorting chamber according to claim 1, comprising a plurality of structures delimiting at least partially the cavity.

12. The sorting chamber according to claim 1, comprising: a spacer, which delimits laterally the internal chamber and connects the base wall and top wall so as to keep the first inner surface and the second inner surface separate from one another; and at least two passages.

13. The sorting chamber according to claim 1, wherein the internal chamber has a volume of from 50 to 100 mm³.

14. A method of sorting leukocytes from erythrocytes comprising using a sorting chamber according to claim 1.

15. The method according to claim 14, comprising: an insertion step, during which a sample is inserted in the chamber; a movement step, during which a relative reciprocating motion is induced between the chamber and the sample; and a sample-taking step, during which a part of the sample is taken; the sample-taking step is subsequent to the movement step.

16. The method according to claim 15, comprising: a centrifuging step, which is subsequent to the sample-taking step and during which the chamber undergoes centrifugation so that the particles of the first type come out of the at least one cavity of the chamber (1); and a recovery step, which is subsequent to the centrifuging step and during which a further part of the sample containing the particles of the first type is taken from the chamber.

17. The method according to claim 16, wherein the chamber comprises at least one passage provided through the base wall; after the centrifuging step, the chamber being held so that the base wall is oriented upwards.

18. The chamber according to claim 1, wherein the wall or column has a width of from 1 µm to 5 µm.

19. The chamber according to claim 1, wherein the wall or column has a width of from 1 µm to 3 µm.

20. A sorting chamber for sorting a sample comprising first particles and second particles, the first particles having at least one dimension smaller than the dimensions of the second particles, and the first and second particles having a major dimension smaller than 1000 µm, the chamber comprising:

a base wall comprising a first inner surface;

a top wall comprising a second inner surface, the top wall being connected to the base wall in a fluid-tight way;

an internal chamber that is at least partially delimited by the base wall and the top wall;

at least one passage that fluidly couples the internal chamber to an external environment;

wherein the base comprises:

a plurality of cavities, each cavity having at least one opening toward the internal chamber and being closed at an end opposite the at least one opening, wherein each cavity is sized to receive and house at least one first particle, but not receive second particles, and the at least one opening of each cavity has substantially the same width, the width of the at least one opening is from 3 µm to 8 µm; and at least one wall or column that at least partially delimits the cavity and has a width of up to 5 µm, wherein the first particles are erythrocytes and the second particles are lymphocytes.

21. The chamber according to claim 1, wherein the chamber is adapted to be moved horizontally in a reciprocating motion.

22. The chamber according to claim 20, wherein the chamber is adapted to be moved horizontally in a reciprocating motion.

23. A method of sorting first particles from second particles present within a sample using the sorting chamber of claim 20 the method comprising: an insertion step, during which a sample is inserted into the chamber; a movement step, during which a relative reciprocating motion is induced between the chamber and the sample; and a sample-taking step, during which a part of the sample is taken; the sample-taking step is subsequent to the movement step.

24. The method according to claim 23, wherein the opening has a width of from 4 to 6 µm.

* * * * *